(12) United States Patent
Cao

(10) Patent No.: US 9,888,853 B2
(45) Date of Patent: Feb. 13, 2018

(54) METHOD FOR MONITORING A PHYSIOLOGICAL CHARACTERISTIC OF HUMAN BODY BASED ON WBAN

(71) Applicant: ZTE CORPORATION, Shenzhen, Guangdong Province (CN)

(72) Inventor: Hua Cao, Shenzhen (CN)

(73) Assignee: ZTE CORPORATION, Shenzhen, Guangdong Province (CN)

(*) Notice: Subject to any disclaimer, the term of this patent is extended or adjusted under 35 U.S.C. 154(b) by 92 days.

(21) Appl. No.: 14/898,461

(22) PCT Filed: Aug. 15, 2013

(86) PCT No.: PCT/CN2013/081594
§ 371 (c)(1),
(2) Date: Dec. 14, 2015

(87) PCT Pub. No.: WO2014/201760
PCT Pub. Date: Dec. 24, 2014

(65) Prior Publication Data
US 2016/0135685 A1    May 19, 2016

(30) Foreign Application Priority Data
Jun. 17, 2013   (CN) .......................... 2013 1 0239515

(51) Int. Cl.
*G08C 17/00*   (2006.01)
*H04L 12/16*   (2006.01)
(Continued)

(52) U.S. Cl.
CPC .......... *A61B 5/0024* (2013.01); *A61B 5/0022* (2013.01); *A61B 5/746* (2013.01);
(Continued)

(58) Field of Classification Search
None
See application file for complete search history.

(56) References Cited

U.S. PATENT DOCUMENTS

2009/0054737 A1* 2/2009 Magar .................. A61B 5/0205
600/300
2010/0094098 A1* 4/2010 Smith .................. A61B 5/0836
600/300

(Continued)

FOREIGN PATENT DOCUMENTS

CN          101674573 A      3/2010
CN          201790809 U      4/2011
(Continued)

OTHER PUBLICATIONS

International Search Report (Form PCT/ISA/210) for PCT/CN2013/081594 dated Aug. 15, 2013.

*Primary Examiner* — Lonnie Sweet
(74) *Attorney, Agent, or Firm* — Koppel, Patrick, Heybl & Philpott

(57) ABSTRACT

The provided are a method and system for monitoring one or more physiological characteristic based on WBAN. The method includes: an node of a micro-network for monitoring the human body acquires physiological characteristic information of the human body; and a hub of the micro-network for monitoring the human body recognizes at least one identifier for identifying a physiological status of the human body according to the acquired physiological characteristic information of the human body, and selects, according to the at least one identifier for identifying the physiological status of the human body, whether to send the physiological characteristic information of the human body to a medical monitoring system terminal via a wireless network or not. According to the method, sign information of the monitored (Continued)

human body may be mastered in first time to provide a strong basis for subsequent treatment.

14 Claims, 2 Drawing Sheets

(51) Int. Cl.
    *H04Q 11/00*     (2006.01)
    *A61B 5/00*     (2006.01)
    *G06F 19/00*     (2011.01)
    *G08B 21/02*     (2006.01)
    *G08B 21/04*     (2006.01)
    *A61B 5/024*     (2006.01)

(52) U.S. Cl.
    CPC ........ *G06F 19/3418* (2013.01); *A61B 5/0002* (2013.01); *A61B 5/02438* (2013.01); *A61B 2505/07* (2013.01); *A61B 2560/0209* (2013.01); *G08B 21/0211* (2013.01); *G08B 21/0277* (2013.01); *G08B 21/0446* (2013.01); *G08B 21/0453* (2013.01)

(56) References Cited

U.S. PATENT DOCUMENTS

| | | | |
|---|---|---|---|
| 2011/0038360 A1* | 2/2011 | Ho | H04J 3/1682 370/346 |
| 2012/0063395 A1* | 3/2012 | Ho | H04W 72/1215 370/329 |
| 2013/0027186 A1* | 1/2013 | Cinbis | A61B 5/0002 340/10.1 |

FOREIGN PATENT DOCUMENTS

| | | |
|---|---|---|
| CN | 102232828 A | 11/2011 |
| CN | 102685233 A | 9/2012 |
| CN | 102968550 A | 3/2013 |
| KR | 2010-0115647 | 10/2010 |
| KR | 2010-0138690 | 12/2010 |
| WO | 2011/153289 | 12/2011 |
| WO | WO 2012/117320 A1 | 9/2012 |
| WO | WO 2012/150534 A1 | 11/2012 |

* cited by examiner

METHOD FOR MONITORING A PHYSIOLOGICAL CHARACTERISTIC OF HUMAN BODY BASED ON WBAN

TECHNICAL FIELD

The disclosure relates to the technical field of Wireless Body Area Network (WBAN), and in particular to a method and system for monitoring in real time one or more physiological characteristics of a human body based on the WBAN.

BACKGROUND

In recent years, along with changes in lifestyles of people, cardiovascular diseases have gradually become one of killers to human health. Major risk factors (for example, hypertension, dyslipidemia, overweight obesity and diabetes) capable of causing incidence of the cardiovascular diseases tend to obviously increase in every region of China, which indicates that incidence of the cardiovascular diseases may further increase in China. Cardiovascular diseases have characteristics of high incidence, high disability rate, high death rate, extremely high treatment cost and the like, so that how to effectively prevent and monitor the cardiovascular diseases becomes a major hotspot and problem in the field of medical treatment.

An existing method for monitoring the cardiovascular diseases mainly depends on professional detection equipment of hospitals, for example, an ElectroCardioGram (ECG) machine and a cardiac colour B-ultrasound machine, but the cardiovascular diseases cannot be monitored for a long time by the method, and for example, for a patient suffering from a cardiovascular disease outbreak, each piece of physiological parameter information of the patient during the outbreak may not be acquired and analyzed in first time, so that treatment may be delayed.

A WBAN technology is a new technology for a short-distance body area network, and unlike other short-distance low-power consumption wireless technologies, the WBAN technology takes application on a human body or in the human body into a special consideration. Usually, the WBAN is a network attached to the human body, and comprises a set of small sensors with a communication function and a body master station (or called a coordinator). Each sensor may be worn on the body, and may also be implanted in the body. The BAN coordinator is a manager of the WBAN as well as a gateway between the WBAN and an external network (for example, a 3rd Generation (3G) network, a Worldwide Interoperability for Microwave Access (WiMAX) network and a Wireless Fidelity (Wi-Fi) network), and may ensure the data to be transmitted and exchanged securely.

SUMMARY

A purpose of the embodiment of the disclosure is to provide a method for monitoring in real time one or more physiological characteristics of a human body based on a Wireless Body Area Network (WBAN).

In order to achieve the purpose of the disclosure, technical solutions of the disclosure are implemented as follows.

A method for monitoring one or more physiological characteristics of a human body based on a Wireless Body Area Network (WBAN) is provided, applied in a micro-network for monitoring the human body based on a WBAN-technology, wherein the micro-network comprises a hub and at least one node arranged on a body surface of a monitored human body or inside the monitored human body, and the method comprises: acquiring, by the node, physiological characteristic information of the human body; and recognizing, by the hub, at least one identifier for identifying a physiological status of the human body according to the acquired physiological characteristic information of the human body, and selecting, by the hub, according to the at least one identifier for identifying the physiological status of the human body, whether to send the physiological characteristic information of the human body to a medical monitoring system terminal via a wireless network or not.

In an example embodiment, the node is activated to acquire the physiological characteristic information of the human body after receiving an instruction of the hub.

In an example embodiment, when the node is not activated by the hub, the following processing is performed respectively: when the node is in an inactive state in a non-wakeup beacon period, the node enters a hibernating state; when the node is in a wakeup beacon period, and is not required to receive a beacon, the node is in the inactive state within transmission time of the beacon; and when the node is not required to transmit a management type frame or a data type frame, the node is in the inactive state in a dedicated access stage and random access stage of a superframe.

In an example embodiment, before the hub and the node exchange a data type frame or a management type frame, mutual discovery is performed between the hub and the node.

In an example embodiment, the mutual discovery comprises mutual discovery between the hub and a disconnected node and mutual discovery between the hub and a connected node, wherein the mutual discovery between the hub and the disconnected node is as follows: before frame transmission between the hub and a disconnected node is performed, the hub ensures that the disconnected node is waken up and is in a same channel with the hub, and then provides a polling allocation interval for the disconnected node; and the mutual discovery between the hub and the connected node is as follows: before frame transmission between the hub and a connected node is performed, the hub sends a wakeup frame and a polling frame to the connected node and provides a polling allocation interval for the connected node.

In an example embodiment, in a process of service interaction between the hub and the node, the hub or the node performs a power control through power adjustment information carried in an interacted frame, to increase or reduce a current power level of an opposite party.

In an example embodiment, the power control is actively initiated by the hub, and when the hub determines that quality of a network link changes, the hub notifies, through power adjustment information carried in a currently interacted frame, the opposite node to change the current power level to be adapted to a current link state.

In an example embodiment, when the node sends data to the hub for multiple times by adopting the same power level, the hub acquires power values of received signals received under the same power level, and compares the power values of the received signals received under the same power level to judge whether the quality of the network link between the hub and the node gets better or gets worse, wherein the hub determines that the quality of the network link gets worse when the power of the received signals gradually decreases; and the hub determines that the quality of the network link gets better when the power of the received signals gradually increases.

In an example embodiment, when the quality of the network link gets worse, the hub notifies, through a downlink, the opposite node to increase a sending power level by at least one level to resist packet loss probably caused by poor link quality; and when the quality of the network link gets better, the hub notifies, through the downlink, the opposite node to reduce the sending power level by at least one level to reduce energy consumption.

In an example embodiment, the power control is actively initiated by the node in one of manners as follows: when the node fails in transmitting a packet after multiple times of packet retransmission, the node actively regulates the current power level; the node actively performs power control according to a preset power control strategy in a process of service interaction with the hub.

In an example embodiment, selecting, by the hub, according to the at least one identifier for identifying the physiological status of the human body, whether to send the physiological characteristic information of the human body to a medical monitoring system terminal via a wireless network or not comprises: acquiring a pre-stored normal physiological value and a pre-stored warning physiological value of the monitored human body according to the identifier for identifying the physiological status of the human body; when the acquired physiological characteristic information of the human body exceeds the normal physiological value, but does not exceed the warning physiological value, storing, by the hub, the current acquired physiological characteristic information of the human body, and/or, sending, by the hub, the current acquired physiological characteristic information of the human body to the medical monitoring system terminal via the wireless network; and when the acquired physiological characteristic information of the human body exceeds the warning physiological value, sending, by the hub, alarming information containing the current acquired physiological characteristic information of the human body to the medical monitoring system terminal via the wireless network.

A system for monitoring one or more physiological characteristics of a human body based on a Wireless Body Area Network (WBAN) is provided, wherein the system comprises: a micro-network for monitoring the human body, configured to acquire physiological characteristic information of the human body, recognize at least one identifier for identifying a physiological status of the human body according to the acquired physiological characteristic information of the human body, and select, according to the at least one identifier for identifying the physiological status of the human body, whether to send the physiological characteristic information of the human body to a medical monitoring system terminal via a wireless network or not; the wireless network, configured to transmit service data; and the medical monitoring system terminal, configured to acquire the physiological characteristic information of a monitored human body from the micro-network monitoring the human body, and perform analysis on the physiological status of the monitored human body according to the physiological characteristic information of the human body.

In an example embodiment, the micro-network for monitoring the human body comprises a hub and at least one node arranged on a body surface of the monitored human body or inside the monitored human body, wherein the node is configured to acquire the physiological characteristic information of the human body; and the hub is configured to recognize the at least one identifier for identifying the physiological status of the human body according to the acquired physiological characteristic information of the human body, and select, according to the at least one identifier for identifying the physiological status of the human body, whether to send the physiological characteristic information of the human body to the medical monitoring system terminal via the wireless network or not.

In an example embodiment, the node is activated to acquire the physiological characteristic information of the human body after receiving an instruction of the hub.

In an example embodiment, when the node is not activated by the hub, the following processing is performed respectively: when the node is in an inactive state in a non-wakeup beacon period, the node enters a hibernating state; when the node is in a wakeup beacon period, and is not required to receive a beacon, the node is in the inactive state within transmission time of the beacon; and when the node is not required to transmit a management type frame or a data type frame, the node is in the inactive state in a dedicated access stage and random access stage of a superframe.

In an example embodiment, before the hub and the node exchange a data type frame or a management type frame, mutual discovery is performed between the hub and the node.

In an example embodiment, the mutual discovery comprises mutual discovery between the hub and a disconnected node and mutual discovery between the hub and a connected node, wherein the mutual discovery between the hub and the disconnected node is as follows: before frame transmission between the hub and a disconnected node is performed, the hub ensures that the disconnected node is waken up and is in a same channel with the hub, and then provides a disconnected polling allocation interval for the disconnected node; and the mutual discovery between the hub and the connected node is as follows: before frame transmission between the hub and a connected node is performed, the hub sends a wakeup frame and a polling frame to the connected node and provides a polling allocation interval for the connected node.

In an example embodiment, in a process of service interaction between the hub and the node, the hub or the node performs a power control through power adjustment information carried in an interacted frame, to increase or reduce a current power level of an opposite party.

In an example embodiment, the power control is actively initiated by the hub, and when the hub determines that quality of a network link changes, the hub notifies, through the power adjustment information carried in the interacted frame, a opposite node to change the current power level to be adapted to a current link state.

In an example embodiment, when the node sends data to the hub for multiple times by adopting the same power level, the hub acquires power values of received signals received under the same power level, and compares the power values the received signals received under the same power level to judge whether the quality of the network link between the hub and the node gets better or gets worse, wherein the hub determines that the quality of the network link gets worse when the power of the received signals gradually decreases; and the hub determines that the quality of the network link gets better when the power of the received signals gradually increases.

In an example embodiment, when the quality of the network link gets worse, the hub notifies, through a downlink, the opposite node to increase a sending power level by at least one level to resist packet loss probably caused by poor link quality through a downlink; and when the quality of the network link gets better, the hub notifies, through the downlink, the opposite node to reduce the sending power level by at least one level to reduce energy consumption.

In an example embodiment, the power control is actively initiated by the node in one of manners as follows: when the node fails in transmitting a packet after multiple times of packet retransmission, the node actively regulates the current power level; the node actively performs power control according to a preset power control strategy in a process of service interaction with the hub.

In an example embodiment, the hub is further configured to acquire a pre-stored normal physiological value and a pre-stored warning physiological value of the monitored human body according to the identifier for identifying the human physiological status of the human body; when the acquired physiological characteristic information of the human body exceeds the normal physiological value, but does not exceed the warning physiological value, the hub is further configured to store the current acquired physiological characteristic information of the human body, and/or, the hub is further configured to send the current acquired physiological characteristic information of the human body to the medical monitoring system terminal via the wireless network; and when the acquired physiological characteristic information of the human body exceeds the warning physiological value, the hub is further configured to send alarming information containing the current acquired physiological characteristic information of the human body to the medical monitoring system terminal via the wireless network.

According to the technical solutions of the disclosure, the physiological characteristic information of the human body of the monitored person is detected in real time through the micro-network for monitoring the human body, and the information is sent to the remote medical monitoring system terminal (for example, a sports and entertainment sign monitoring terminal, an emergency call terminal, a monitoring terminal, a medical server terminal and a remote treatment terminal) through a certain processing mechanism, so that sign information of the monitored person may be mastered in first time to provide a strong basis for subsequent treatment.

Achievement of the purpose, function characteristics and good effects of the disclosure are further described below with reference to specific embodiments and the drawings.

DETAILED DESCRIPTION OF THE EMBODIMENTS

The technical solutions of the disclosure are further described below with reference to the drawings and specific embodiments in detail, so as to make those skilled in the art better understand and implement the disclosure, but the enumerated embodiments are not intended to limit the disclosure.

A method for monitoring one or more physiological characteristics of a human body based on a WBAN is provided in the embodiment of the present disclosure, and a micro-network for monitoring the human body based on a WBAN-technology includes a hub and at least one node arranged on a body surface of a monitored human body or inside the monitored human body, wherein the method includes:

Step 10: the node acquires physiological characteristic information of the human body; and Step 20: the hub recognizes at least one identifier for identifying a physiological status of the human body according to the acquired physiological characteristic information of the human body, and selects, according to the at least one identifier for identifying physiological status of the human body, whether to send the physiological characteristic information of the human body to a medical monitoring system terminal via a wireless network or not.

The monitored physiological characteristics of the human body include all physiological characteristics for diagnosing related diseases of the human body.

A corresponding relationship between each physiological characteristic of the human body and a corresponding identifier for identifying the physiological status of the human body is pre-recorded in the system, wherein the identifier for identifying the physiological status of the human body is used to judge the status of the human body by combining with the actually received physiological characteristic data of the human body, and for example, the identifier for identifying the physiological status of the human body is provided in the embodiment of the disclosure. Each piece of physiological data of the monitored human body in a normal status is pre-acquired and stored, then the physiological data of the monitored human body in an abnormal or morbid status is acquired, and a normal value threshold and a warning value threshold for identifying whether the human body is normal or not is set according to the physiological data in the normal status and the physiological data in the abnormal or morbid status, and the status of the monitored human body is judged according to whether the acquired physiological data exceeds the normal value threshold or the warning value threshold.

Figure 1:
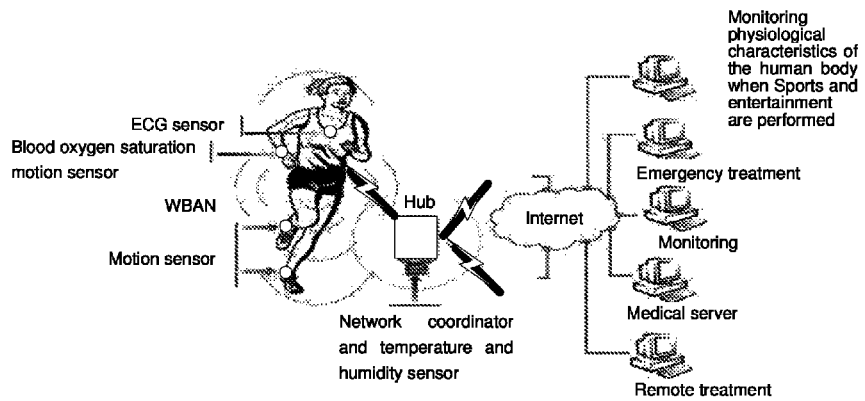
FIG. 1 is a structure diagram of a system for monitoring one or more physiological characteristics of a human body based on a WBAN according to an embodiment of the disclosure.

For example, a method for monitoring the cardiovascular disease based on the WBAN is provided in the embodiment of the disclosure. As shown in FIG. 1, the system applied for the above method mainly includes the micro-network for monitoring the human body based on the WBAN technology, the wireless network and the medical monitoring system terminal. The micro-network for monitoring the human body comprises the node and the hub. The micro-network for monitoring the human body comprises and only comprises one hub, and the hub is used to regulate media access and performs power management. The node is located on the body surface of the monitored human body or in the monitored human body, and includes various kinds of sensor device, such as an ECG sensor and a motion sensor. These sensors are activated to start acquiring the human physiological characteristic information after receiving instructions of the hub.

Under normal circumstances, the node may be in two different states, i.e. a hibernating state and a dormant state, according to arrangement of the hub. For example: when the node is in an inactive state in a non-wakeup beacon period, the node "hibernates"; when the node is in a wakeup beacon period, and is not required to receive a beacon, the node is in the inactive state transmission time of the beacon; and when the node is not required to transmit a management type frame or data type frame, the node is in the inactive state in a dedicated access stage and random access stage of a superframe, namely enters the dormant state.

Before the hub and the node exchange the data type frame or the management type frame, mutual discovery is performed between the hub and the node. In the embodiment of the disclosure, two implementation manners are mainly adopted: mutual discovery between the hub and a disconnected node and mutual discovery between the hub and a connected node.

For the mutual discovery between the hub and a disconnected node, before frame transmission between the hub and the disconnected node, the hub ensures that the disconnected node is waken up and is in the same channel with the hub, and then provides a disconnected polling allocation interval for the disconnected node.

For the mutual discovery between the hub and a connected node, before frame transmission between the hub and the connected node, the hub also sends a wakeup frame and a polling frame and provides a polling allocation interval for the connected node.

In order to support managing the energy of the WBAN and fulfill the aim of long-term use, each communication node may have two basic functions: one is necessary preparation for the node to be in dormancy state, for example, storing a working state before dormancy; and the other is to switch the node to a dormant state or a wakeup state within a preset time.

In consideration of energy saving and safety of the human body, sending power of a node for transmitting information is optimized by power control, that is: when a channel condition gets worse, the sending power of the node is increased to ensure correct reception of a data packet on the premise of ensuring that radiation power is within a safety range; and when the channel condition meets the requirement of transmission reliability, the sending power of the node may be properly reduced to save energy, prolong working life of the node and further prolong lifetime of the network. In a process of service interaction between the node and the hub, the node or the hub may perform power control through information in an interacting frame, thereby increasing or reducing a current power level whenever power control is required (the quality of the channel communication get better or worse) either in a competition period or a non-competition period.

Adjustment of the power level may be initiated by the hub, and may also be initiated by the node. The following two triggering mechanisms are mainly adopted:

1) the hub actively initiates power control: the hub actively initiates the power control mainly refers to that, when the hub judges that the quality of a network link changes, the hub, interacts with the node through the frame, and notifies the node to change the power level to be adapted to a current link state. In an optional manner, when the node sends data to the hub for multiple times by adopting the same power level, the hub records the power values of received signals received under the same power level, and compares the power values of the signals under the same power level to judge whether the quality of the network link between the hub and the node is improved or reduced. When the power of the received signals gradually decreases, it is indicated that the quality of the link get worse, and the hub notifies the node to increase the sending power level by one level (not lower than a maximum power level) to resist packet loss probably caused by poor link quality through a downlink; and when the power of the received signals gradually increases, it is indicated that the quality of the link get better, and at this time, the hub notifies the node to reduce the sending power level by one level (not lower than a minimum power level) to reduce energy and prolong life of the node through the downlink.

2) the node actively initiates power control: the node actively initiates power control mainly refers to that the node changes the current power level when the node still fails after multiple packet retransmission, or actively performs power control according to a preset power control strategy (for example, periodically).

The physiological characteristic information of the human body acquired by the sensors on the node is transmitted to the hub, arranged by the hub and transmitted through the wireless network, and then the physiological data acquired by the micro-network for monitoring the human body is uploaded to the medical monitoring system terminal through the wireless network.

In the embodiment, the hub pre-stores various types of physiological information of the monitored person acquired in the normal status, sets the warming value, and may compare the physiological data acquired in real time with the stored normal value and the warning value for analysis, and when receiving abnormal physiological data, give an alarm to the monitored person and give a report to the medical monitoring system terminal. In a optional manner: when the acquired physiological characteristic information of the human body exceeds the normal physiological value (i.e., the above normal value), but does not exceed the warning physiological value (i.e., the above warning value), the hub is configured to store the current acquired physiological characteristic information of the human body, and/or, the hub is configured to send the current acquired physiological characteristic information of the human body to the medical monitoring system terminal via the wireless network; and when the acquired physiological characteristic information of the human body exceeds the warning physiological value, the hub is configured to send alarming information containing the current acquired physiological characteristic information of the human body to the medical monitoring system terminal via the wireless network.

The medical monitoring system terminal is located in a primary medical station or a specialized hospital, and includes emergency treatment, remote treatment and the like. The medical monitoring system terminal is connected with the micro-network for monitoring the human body via the Internet. These medical monitoring system terminal processes the acquired information, gives a prompt and a suggestion when a potential risk factor of the monitored person increases, performs proper treatment under operation of a professional, and may rapidly give a response to save precious treatment time particularly in case of an outbreak.

In the embodiment, the micro-network for monitoring the human body comprises and only comprises one hub, and regulates media access and performs power management through the hub. In order to reduce power consumption, the sensors on the node enter the hibernating state or the dormant state according to the arrangement of the hub under normal circumstances, the sensors are activated to start acquiring physiological signals of the human body after receiving the instructions of the hub, and the acquired physiological data (i.e., the above physiological signals) is transmitted to the hub by the node in a wireless transmission manner.

The hub pre-stores various types of physiological characteristic information of the monitored person acquired in the normal status, sets the normal value and the warming value according to the physiological characteristic information, and may compare each piece of real-time physiological data acquired in real time with the stored normal value and warning value for analysis. For example, during ECG examination, a heart rate of a child is higher, and right ventricular preponderance is reflected in Quantum Resonance Spectrography (QRS). The data is stored in the hub, and when an ECG signal with right ventricular preponderance is acquired, the hub determines that the ECG signal is normal, and may not give an alarm and repeatedly activate an ECG sensor on the node side to acquire the signal, so that power consumption is reduced, and the aim of long-term monitoring is fulfilled; and an alarming signal containing the real-time physiological data is generated and sent to the remote medical monitoring system terminal once the preset warning value is exceeded. This is significant for sensors which are implanted in the human body and of which power supplies are difficult to be replaced.

Figure 2:
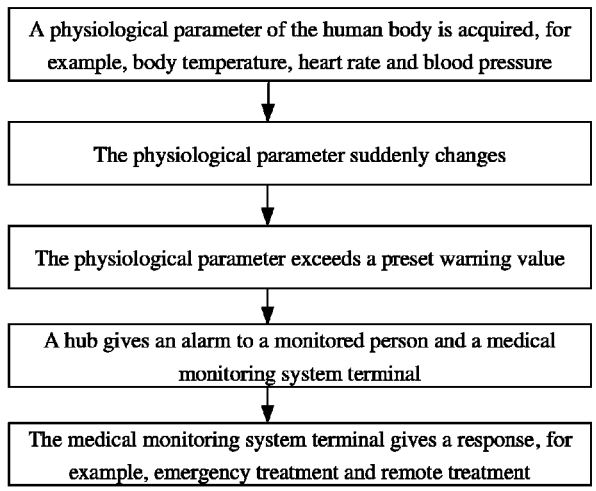
FIG. 2 is a flowchart of alarming and emergency processing for a sudden disease according to an embodiment of the disclosure.

On the basis of the method, a paroxysmal disease may be alarmed and emergently treated. Most of congenital or acquired cardiovascular disease patients are unaware of own potential risks, which may even cause sudden death during strenuous exercises. As shown in FIG. 2, the physiological data acquired by the sensors is transmitted to the hub, and when the hub determines that the acquired physiological data exceeds a certain warning value, the hub sets an alarm to prompt the monitored person or the medical monitoring system terminal, and the medical monitoring system terminal gives a response to the paroxysmal disease, and may arrange emergency admission and related treatment according to a specific condition.

Figure 3:
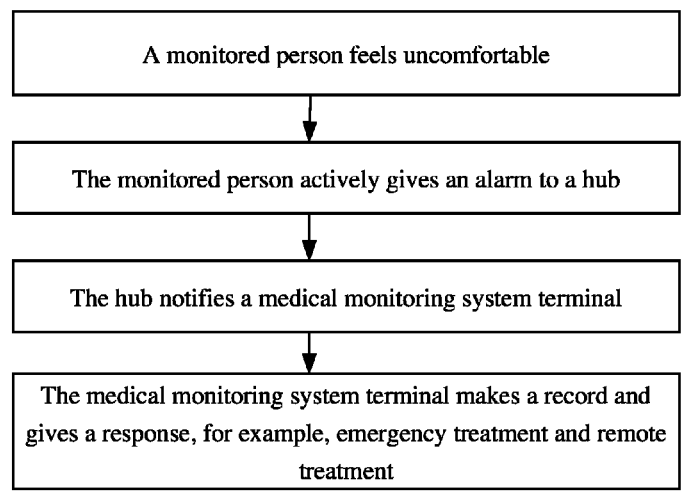
FIG. 3 is a flowchart of emergency processing under a condition of active alarming of a monitored person according to an embodiment of the disclosure.

On the basis of the system, the monitored person may actively alarm and treat own condition. As shown in FIG. 3, when feeling palpitation, dyspnea, oppression in chest, vertigo, giddiness, heart complain, precordial pain or the like, a patient suffering from a cardiovascular disease may give an alarm through the hub worn on him/her, and then the medical monitoring system terminal increases his/her priority and arranges related specialized examination and treatment according to an acquired physiological information condition. If the patient has been emergently treated by himself/herself, for example, taking a first-aid medicament monarkite for stable angina, the hub and the medical monitoring system terminal may record accurate time and manner for such a condition for distinguishing data acquired later for use during the disease diagnosis of a doctor.

Also as shown in FIG. 1, a system for monitoring the physiological characteristic of the human body based on WBAN is provided in the embodiment of the present disclosure, which includes:

a micro-network for monitoring the human body, configured to acquire physiological characteristic information of the human body, recognize at least one identifier for identifying a physiological status of the human body according to the acquired physiological characteristic information of the human body, and select, according to the at least one identifier for identifying the physiological status of the human body, whether to send the physiological characteristic information of the human body to a medical monitoring system terminal via a wireless network or not; the wireless network, configured to transmit service data; and the medical monitoring system terminal, configured to acquire the physiological characteristic information of the human body of a monitored person from the micro-network for monitoring the human body, and perform physiological status analysis on the monitored person according to the physiological characteristic information of the human body.

In the embodiment, the micro-network for monitoring the human body includes a hub and at least one node arranged on a body surface of the monitored human body or inside the monitored human body, wherein the node is configured to acquire the physiological characteristic information of the human body; and the hub is configured to recognize the at least one identifier for identifying the physiological status of the human body according to the acquired physiological characteristic information of the human body, and select, according to the at least one identifier for identifying physiological status of the human body, whether to send the physiological characteristic information of the human body to the medical monitoring system terminal via the wireless network or not.

In the embodiment, the node is activated to acquire the physiological characteristic information of the human body after receiving an instruction of the hub. In an example implementation mode, when the node is not activated by the hub, the following processing is performed respectively: when the node is in an inactive state in a non-wakeup beacon period, the node enters a hibernating state; when the node is in a wakeup beacon period, and is not required to receive a beacon, the node is in the inactive state during transmitting the beacon; and when the node is not required to transmit a management or data type frame, the node is in the inactive state in a dedicated access stage and random access stage of a superframe.

In the embodiment, before the hub and the node exchange the data type frame or the management type frame, mutual discovery is performed between the hub and the node, wherein the mutual discovery includes mutual discovery between the hub and disconnected nodes and mutual discovery between the hub and connected nodes, and preferably, the mutual discovery with the disconnected nodes is as follows: before frame transmission between the hub and the disconnected node, the hub ensures that the disconnected node is waken up and is in the same channel with the hub, and then provides a disconnected polling allocation interval for the disconnected node; and the mutual discovery between the hub and the connected nodes is as follows: before frame transmission between the hub and the connected node, the hub sends a wakeup frame and a polling frame to the connected node and provides a polling allocation interval for the connected node.

In the embodiment, in a process of service interaction between the hub and the node, the hub or the node may perform power control through power adjustment information in an interacting frame, thereby increasing or reducing a current power level of the opposite party.

Wherein, power control is actively initiated by the hub, and when the hub judges that quality of a network link changes, the hub notifies, through the power adjustment information in the interacting frame, the opposite node to change the power level to be adapted to a current link state. Preferably, when the node sends data to the hub for multiple times by adopting the same power level, the hub acquires the power values of signals received under the same power level, and compares the power values of the signals under the same power level to judge whether the quality of the network link between the hub and the node is improved or reduced, wherein the hub determines that the quality of the network link is reduced if the power of the received signals gradually decreases; and the hub determines that the quality of the network link is improved if the power of the received signals gradually increases.

For how to regulate the power level by the hub, preferably: when the quality of the network link get worse, the hub notifies the opposite node to increase the sending power level by at least one level to resist packet loss probably caused by poor link quality through a downlink; and when the quality of the network link is improved, the hub notifies the opposite node to reduce the sending power level by at least one level to reduce energy consumption through the downlink.

In another embodiment, power control is actively initiated by the node in manners as follows:

1: when the node still fails after multiple packet retransmission, the node actively regulates the current power level; or, 2: the node actively performs power control according to a preset power control strategy in the process of service interaction with the hub.

In the embodiment, the hub is further configured to acquire a pre-stored normal physiological value and warning physiological value of the monitored human body according to the identifier for identifying the physiological status of the human body; when the acquired physiological characteristic information of the human body exceeds the normal physiological value, but does not exceed the warning physiological value, the hub is further configured to store the current acquired physiological characteristic information of the human body, and/or, the hub is further configured to send the current acquired physiological characteristic information of the human body to the medical monitoring system terminal via the wireless network; and when the acquired physiological characteristic information of the human body exceeds the warning physiological value, the hub is further configured to send alarming information containing the current acquired physiological characteristic information of the human body to the medical monitoring system terminal via the wireless network.

The above is only the example embodiment of the disclosure and not thus intended to limit the scope of the disclosure. Equivalent structure or equivalent flow transformation made by virtue of the Specification and contents of the drawings of the disclosure, or direct or indirect application of the Specification and contents of the drawings of the disclosure to other related arts shall fall within the scope of protection of the disclosure.

What is claimed is:

1. A method for monitoring one or more physiological characteristics of a human body based on a Wireless Body Area Network (WBAN), applied in a micro-network for monitoring the human body based on a WBAN-technology, wherein the micro-network comprises a hub and at least one node arranged on a body surface of a monitored human body or inside the monitored human body, and the method comprises:

acquiring, by the node, physiological characteristic information of the human body; and recognizing, by the hub, at least one identifier for identifying a physiological status of the human body according to the acquired physiological characteristic information of the human body, and selecting, by the hub, according to the at least one identifier for identifying the physiological status of the human body, whether to send the physiological characteristic information of the human body to a medical monitoring system terminal via a wireless network or not;

wherein the node is activated to acquire the physiological characteristic information of the human body after receiving an instruction of the hub;

wherein, when the node is not activated by the hub, the following processing is performed respectively:

when the node is in an inactive state in a non-wakeup beacon period, the node enters a hibernating state; when the node is in a wakeup beacon period, and is not required to receive a beacon, the node is in the inactive state within transmission time of the beacon; and when the node is not required to transmit a management type frame or a data type frame, the node is in the inactive state in a dedicated access stage and random access stage of a superframe.

2. The method as claimed in claim 1, wherein, before the hub and the node exchange a data type frame or a management type frame, mutual discovery is performed between the hub and the node, wherein the mutual discovery comprises mutual discovery between the hub and a disconnected node and mutual discovery between the hub and a connected node, wherein the mutual discovery between the hub and the disconnected node is as follows: before frame transmission between the hub and a disconnected node is performed, the hub ensures that the disconnected node is waken up and is in a same channel with the hub, and then provides a polling allocation interval for the disconnected node; and the mutual discovery between the hub and the connected node is as follows: before frame transmission between the hub and a connected node is performed, the hub sends a wakeup frame and a polling frame to the connected node and provides a polling allocation interval for the connected node.

3. The method as claimed in claim 1, wherein, in a process of service interaction between the hub and the node, the hub or the node performs a power control through power adjustment information carried in an interacted frame, to increase or reduce a current power level of an opposite party.

4. The method as claimed in claim 3, wherein the power control is actively initiated by the hub, and when the hub determines that quality of a network link changes, the hub notifies, through power adjustment information carried in a currently interacted frame, the opposite node to change the current power level to be adapted to a current link state; or, the power control is actively initiated by the node in one of manners as follows: when the node fails in transmitting a packet after multiple times of packet retransmission, the node actively regulates the current power level; the node actively performs power control according to a preset power control strategy in a process of service interaction with the hub.

5. The method as claimed in claim 4, wherein, when the node sends data to the hub for multiple times by adopting the same power level, the hub acquires power values of received signals received under the same power level, and compares the power values of the received signals received under the same power level to judge whether the quality of the network link between the hub and the node gets better or gets worse, wherein the hub determines that the quality of the network link gets worse when the power of the received signals gradually decreases; and the hub determines that the quality of the network link gets better when the power of the received signals gradually increases.

6. The method as claimed in claim 5, wherein, when the quality of the network link gets worse, the hub notifies, through a downlink, the opposite node to increase a sending power level by at least one level to resist packet loss probably caused by poor link quality; and when the quality of the network link gets better, the hub notifies, through the downlink, the opposite node to reduce the sending power level by at least one level to reduce energy consumption.

7. The method as claimed in claim 1, wherein selecting, by the hub, according to the at least one identifier for identifying the physiological status of the human body, whether to send the physiological characteristic information of the human body to a medical monitoring system terminal via a wireless network or not comprises:

acquiring a pre-stored normal physiological value and a pre-stored warning physiological value of the monitored human body according to the identifier for identifying the physiological status of the human body;

when the acquired physiological characteristic information of the human body exceeds the normal physiological value, but does not exceed the warning physiological value, storing, by the hub, the current acquired physiological characteristic information of the human body, and/or, sending, by the hub, the current acquired physiological characteristic information of the human body to the medical monitoring system terminal via the wireless network; and when the acquired physiological characteristic information of the human body exceeds the warning physiological value, sending, by the hub, alarming information containing the current acquired physiological characteristic information of the human body to the medical monitoring system terminal via the wireless network.

8. A system for monitoring one or more physiological characteristics of a human body based on a Wireless Body Area Network (WBAN), wherein the system comprises:

a micro-network for monitoring the human body, configured to acquire physiological characteristic information of the human body, recognize at least one identifier for identifying a physiological status of the human body according to the acquired physiological characteristic information of the human body, and select, according to the at least one identifier for identifying the physiological status of the human body, whether to send the physiological characteristic information of the human body to a medical monitoring system terminal via a wireless network or not;

the wireless network, configured to transmit service data; and the medical monitoring system terminal, configured to acquire the physiological characteristic information of a monitored human body from the micro-network monitoring the human body, and perform analysis on the physiological status of the monitored human body according to the physiological characteristic information of the human body;

wherein the system comprises a hardware processor, configured to perform programming nodes stored in a memory, wherein the programming nodes comprise: a hub and at least one node arranged on a body surface of the monitored human body or inside the monitored human body, wherein the node is configured to acquire the physiological characteristic information of the human body; and the hub is configured to recognize the at least one identifier for identifying the physiological status of the human body according to the acquired physiological characteristic information of the human body, and select, according to the at least one identifier for identifying the physiological status of the human body, whether to send the physiological characteristic information of the human body to the medical monitoring system terminal via the wireless network or not;

wherein the node is activated to acquire the physiological characteristic information of the human body after receiving an instruction of the hub; wherein, when the node is not activated by the hub, the following processing is performed respectively: when the node is in an inactive state in a non-wakeup beacon period, the node enters a hibernating state; when the node is in a wakeup beacon period, and is not required to receive a beacon, the node is in the inactive state within transmission time of the beacon; and when the node is not required to transmit a management type frame or a data type frame, the node is in the inactive state in a dedicated access stage and random access stage of a superframe.

9. The system as claimed in claim 8, wherein, before the hub and the node exchange a data type frame or a management type frame, mutual discovery is performed between the hub and the node, wherein the mutual discovery comprises mutual discovery between the hub and a disconnected node and mutual discovery between the hub and a connected node, wherein the mutual discovery between the hub and the disconnected node is as follows: before frame transmission between the hub and a disconnected node is performed, the hub ensures that the disconnected node is waken up and is in a same channel with the hub, and then provides a disconnected polling allocation interval for the disconnected node; and the mutual discovery between the hub and the connected node is as follows: before frame transmission between the hub and a connected node is performed, the hub sends a wakeup frame and a polling frame to the connected node and provides a polling allocation interval for the connected node.

10. The system as claimed in claim 8, wherein, in a process of service interaction between the hub and the node, the hub or the node performs a power control through power adjustment information carried in an interacted frame, to increase or reduce a current power level of an opposite party.

11. The system as claimed in claim 10, wherein the power control is actively initiated by the hub, and when the hub determines that quality of a network link changes, the hub notifies, through the power adjustment information carried in the interacted frame, an opposite node to change the current power level to be adapted to a current link state; or, the power control is actively initiated by the node in one of manners as follows: when the node fails in transmitting a packet after multiple times of packet retransmission, the node actively regulates the current power level; the node actively performs power control according to a preset power control strategy in a process of service interaction with the hub.

12. The system as claimed in claim 11, wherein, when the node sends data to the hub for multiple times by adopting the same power level, the hub acquires power values of received signals received under the same power level, and compares the power values the received signals received under the same power level to judge whether the quality of the network link between the hub and the node gets better or gets worse, wherein the hub determines that the quality of the network link gets worse when the power of the received signals gradually decreases; and the hub determines that the quality of the network link gets better when the power of the received signals gradually increases.

13. The system as claimed in claim 12, wherein, when the quality of the network link gets worse, the hub notifies, through a downlink, the opposite node to increase a sending power level by at least one level to resist packet loss probably caused by poor link quality through a downlink; and when the quality of the network link gets better, the hub notifies, through the downlink, the opposite node to reduce the sending power level by at least one level to reduce energy consumption.

14. The system as claimed in claim 8, wherein the hub is further configured to acquire a pre-stored normal physiological value and a pre-stored warning physiological value of the monitored human body according to the identifier for identifying the human physiological status of the human body;

when the acquired physiological characteristic information of the human body exceeds the normal physiological value, but does not exceed the warning physiological value, the hub is further configured to store the current acquired physiological characteristic information of the human body, and/or, the hub is further configured to send the current acquired physiological characteristic information of the human body to the medical monitoring system terminal via the wireless network; and when the acquired physiological characteristic information of the human body exceeds the warning physiological value, the hub is further configured to send alarming information containing the current acquired physiological characteristic information of the human body to the medical monitoring system terminal via the wireless network.

* * * * *